(12) United States Patent
Avagyan et al.

(10) Patent No.: US 12,390,355 B2
(45) Date of Patent: Aug. 19, 2025

(54) PORTABLE THORACIC BRACE WITH SPINAL TRACTION AND METHOD

(71) Applicant: CORESTRAIGHT LTD., Ajax (CA)

(72) Inventors: Armen Avagyan, Ajax (CA); Primoz Cresnik, Milton (CA); Brian Petz, Ancaster (CA)

(73) Assignee: CORESTRAIGHT LTD., Ontario (CA)

( * ) Notice: Subject to any disclaimer, the term of this patent is extended or adjusted under 35 U.S.C. 154(b) by 200 days.

(21) Appl. No.: 18/241,357

(22) Filed: Sep. 1, 2023

(65) Prior Publication Data

US 2024/0074887 A1 Mar. 7, 2024

Related U.S. Application Data

(60) Provisional application No. 63/403,464, filed on Sep. 2, 2022.

(51) Int. Cl.
*A61F 5/02* (2006.01)
*A61F 5/048* (2006.01)

(52) U.S. Cl.
CPC .............. *A61F 5/028* (2013.01); *A61F 5/048* (2013.01)

(58) Field of Classification Search
CPC .. A61F 5/024; A61F 5/028; A61F 5/04; A61F 5/048; A61H 1/0218; A61H 1/0292; A61H 2201/165; A61H 2201/1623; A61H 2201/1697; A61H 2201/1436; A61H 2201/1628; A61H 2201/1238; A61H 2201/1664; A61H 2201/1207; A61H 2201/1645; A61H 2201/1253
USPC .......................................................... 602/19
See application file for complete search history.

(56) References Cited

U.S. PATENT DOCUMENTS

2016/0296361 A1* 10/2016 Leake .................. A61H 1/0292

* cited by examiner

*Primary Examiner* — Alireza Nia
*Assistant Examiner* — Daniel A Miller
(74) *Attorney, Agent, or Firm* — Perry + Currier Inc

(57) ABSTRACT

A wearable traction device includes: a traction rod including a superior segment, and an inferior segment; a lower anchoring assembly coupled to the inferior segment of the traction rod, the lower anchoring assembly configured for affixing to a lower torso of a user; an upper anchoring assembly movably coupled to the superior segment of the traction rod, the upper anchoring assembly configured for affixing to an upper torso of a user; a releasable lock supported on the upper anchoring assembly, the lock having: (i) an engaged position configured to permit movement of the upper anchoring assembly in a superior direction along the superior segment of the traction rod, and prevent movement of the upper anchoring assembly in an inferior direction along the superior segment, and (ii) a disengaged position configured to permit movement of the upper anchoring assembly in the superior and inferior directions.

10 Claims, 5 Drawing Sheets

PORTABLE THORACIC BRACE WITH SPINAL TRACTION AND METHOD

CROSS-REFERENCE TO RELATED APPLICATIONS

This application claims priority to U.S. Provisional Patent Application No. 63/403,464, filed Sep. 2, 2022, the contents of which are incorporated herein by reference.

FIELD

The present invention relates to a thoracic brace, and more particularly to a thoracic brace that applies spinal traction resulting in spinal decompression.

BACKGROUND

Back problems are a significant issue for much of the human population; consider that eight out of 10 American will experience back pain in their lifetime. According to Global Burden of Disease Study 2017 (Institute for Health Metrics and Evaluation (IHME), *Findings from the Global Burden of Disease Study* 2017, Seattle, WA: IHME, 2018), back pain is a leading cause of disability worldwide and prevents people from working and doing everyday simple activities. Research by the Mayo Clinic also found that back problems are the third most common reason for a visit to the doctor's office.

Conventional consumer back braces may provide limited support for the spine, e.g., limited to lumbar or lumbar and partial thoracic support. These braces and supports are typically designed from plastics and fabrics and are designed for all day use. Other long-term wear braces exist to treat spinal curvature conditions (scoliosis or kyphosis) and are not suitable for relieving pain from chronic conditions such as sciatica, or herniated or bulging disc. Devices that apply traction to a user's spine may have bed-like form factors, and the use of such devices may therefore involve lying down and being restrained against the device, impeding or preventing other activities. Such devices may also be complex and costly.

SUMMARY

An aspect of the specification provides a wearable traction device, comprising: a traction rod including a superior segment, and an inferior segment; a lower anchoring assembly coupled to the inferior segment of the traction rod, the lower anchoring assembly configured for affixing to a lower torso of a user; an upper anchoring assembly movably coupled to the superior segment of the traction rod, the upper anchoring assembly configured for affixing to an upper torso of a user; a releasable lock supported on the upper anchoring assembly, the lock having: (i) an engaged position configured to permit movement of the upper anchoring assembly in a superior direction along the superior segment of the traction rod, and prevent movement of the upper anchoring assembly in an inferior direction along the superior segment, and (ii) a disengaged position configured to permit movement of the upper anchoring assembly in the superior and inferior directions.

BRIEF DESCRIPTIONS OF THE DRAWINGS

Embodiments are described with reference to the following figures.

DETAILED DESCRIPTION

Figure 1:
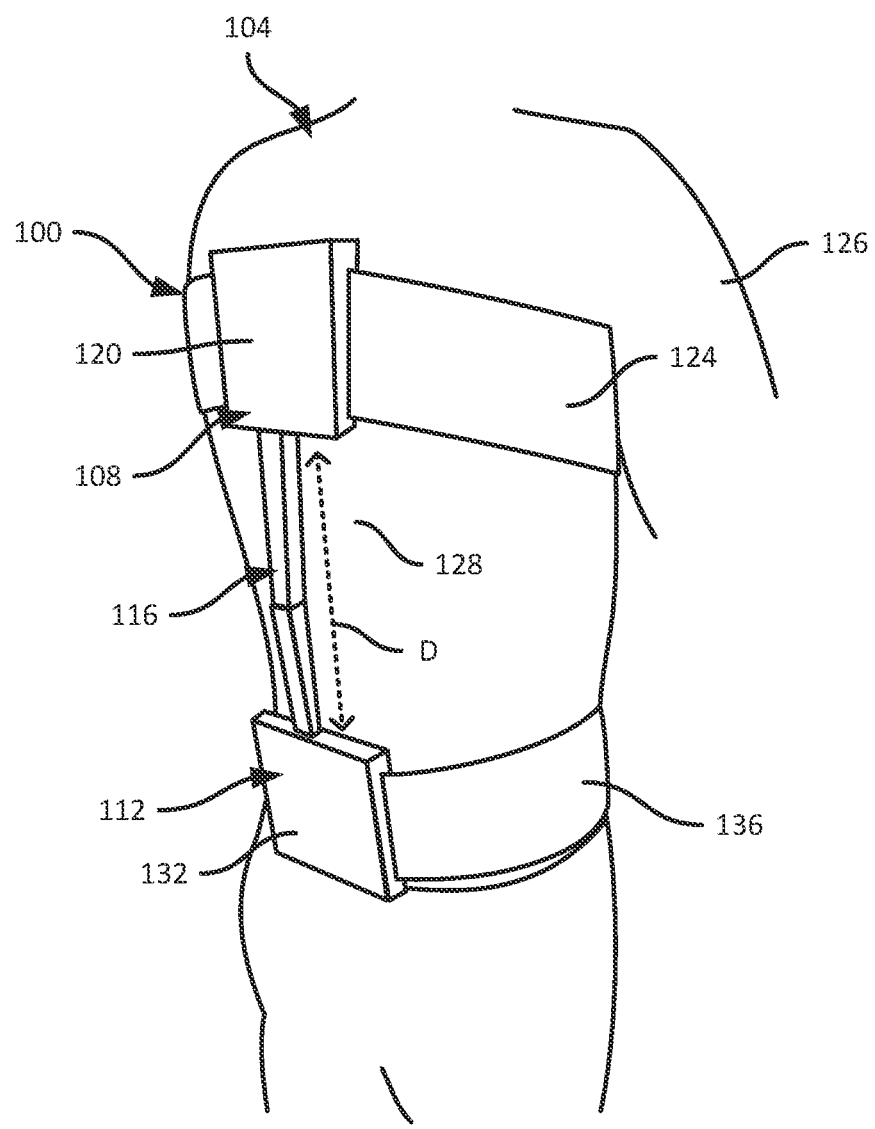
FIG. 1 is a diagram of a wearable traction device worn by a user.

FIG. 1 depicts a wearable traction device 100 (also referred to herein as the device 100) in an operational configuration, e.g., worn by a user 104. The device 100 includes an upper anchoring assembly 108, a lower anchoring assembly 112, and a traction rod 116 (which may also be referred to as the decompression rod 116) extending between the anchoring assemblies 108 and 112. The upper anchoring assembly 108, in this example, includes a traction plate 120 and a belt 124. The plate 120 is configured to rest against a back 128 of the user 104, and the belt 124 is configured to encircle the torso of the user 104, e.g., under the arms 126 of the user 104 to wrap around the chest, to substantially affix the plate 120 in the illustrated position (e.g., to mitigate or prevent movement of the plate 120 relative to the back 128).

The lower anchoring assembly 112 includes a traction plate 132 configured to rest against the back 128, and a belt 136 configured to encircle the torso of the user 104, e.g., at or near the waist of the user 104, to substantially affix the plate 132 in the illustrated position. The belts 124 and 136 can include Velcro, buckles, or other adjustment mechanisms to accommodate various torso sizes. The belts 124 and 136 can further include pouches or the like to receive one or more reinforcing plates. For example, the belts 124 and 136 can include nylon or other textile belts, configured to receive reinforcing plates of plastic (e.g., ABS or the like). In other examples, such reinforcing plates can be omitted, e.g., if the belts 124 and/or 136 are sufficiently rigid. For example, a segmented metal belt, a leather belt, or the like, may have sufficient stiffness to avoid the need for reinforcement.

The upper anchoring assembly 108, in other words, is configured to affix to an upper torso of the user 104, e.g., placing the plate 120 adjacent to thoracic vertebrae (e.g., T5 and/or T6, although the exact position of the plate 120 may vary). The lower anchoring assembly 112, meanwhile, is configured to affix to a lower torso of the user 104, e.g., placing the plate 132 adjacent to the lumbar vertebrae and/or sacrum of the user 104. As described below in greater detail, the positions of either or both of the anchoring assemblies 108 and 112 along the traction rod 116 can be adjusted to increase a distance "D" between the plates 120 and 132. Engagement between the anchoring assemblies 108 and 112 and the traction rod 116 serves to maintain a set distance D between the anchoring assemblies 108 and 112, resisting or preventing a reduction in the distance D during use of the device 100.

Affixing of the anchoring assemblies 108 and 112 to the user 104, coupled with maintenance of the distance D via the traction rod 116, therefore enables the device 100 to apply traction to a portion of the spine of the user 104. Application of traction by the device 100 can decompress the spinal column of the user 104, which may relieve pain from various conditions (e.g., compressed nerve roots, joints, and related tissues), while the device 100 is worn and for a period of time (e.g., hours to days) after the device 100 is removed. Further, as discussed below, the device 100 can be operated by the user 104 with little or no assistance from third parties, and because the device 100 is wearable, the user 104 may remain mobile while wearing the device 100, rather than being restricted to a fixed location, as is the case with certain other spinal traction devices.

Figure 2:
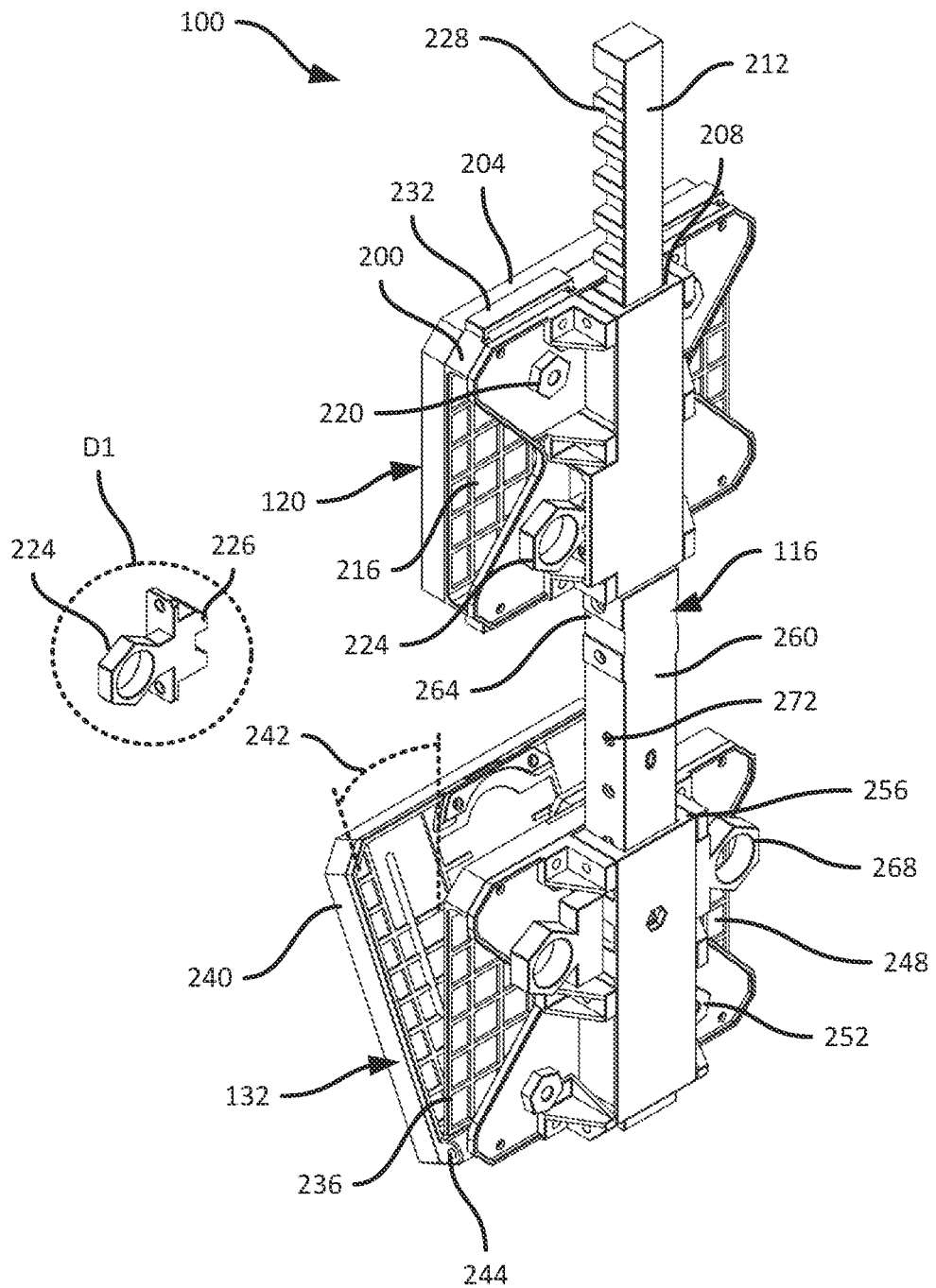
FIG. 2 is an isometric view of the wearable traction device in isolation.

Turning to FIG. 2, an example embodiment of the device 100 is shown in isolation, with the belts 124 and 136 omitted. As shown in FIG. 2, the traction plate 120 of the upper anchoring assembly 108 includes a base 200 supporting a pad 204. The base 200 can be fabricated from a suitable plastic, metal, composite, or the like, and couples the plate 120 to the traction rod 116. In particular, the base 200 defines a channel 208 through which a superior segment 212 (e.g., upper, towards the head of the user 104 when the device 100 is in use) of the rod 116 is received.

The base 200 also defines a raceway 216 or other form of channel therethrough, for receiving the belt 124. The base 200 can support one or more locking screws 220 (two are shown in this example) to secure the belt 124 within the raceway 216 (e.g., by extending into the raceway 216 and pinning the belt 124 against the other side of the raceway 216). In other examples, the belts 124 and/or 136 can include distinct pieces or sections coupled to either side of the plates 120 and 132 respectively, rather than one piece or section that traverses the corresponding plate 120 or 132 via a raceway such as the raceway 216.

The pad 204 can be formed from a suitable foam, rubber, or the like, e.g., with a lower stiffness than the material forming the base 200. The pad 204 is configured to rest directly against the back 128 of the user 104 (not necessarily in contact with skin, e.g., over the user's clothing). In the illustrated example, the surface of the pad 204 configured to contact the user's back 128 is planar, but in other examples the pad 204 can have a curved surface for user comfort.

The device 100 also includes a releasable lock 224. The lock 224 is supported on the upper anchoring assembly 108 (e.g., by the member defining the channel 208), and specifically on the base 200 in this example. The lock 224, as shown in the detail view D1 includes, one or more protrusions 226 that extend into the channel 208 to engage with a ratchet 228 (e.g., a linear gear) defined on the superior segment 212 of the rod 116. The lock 224 has an engaged position (illustrated in FIG. 2), in which the lock 224 is engaged with the ratchet 228, and prevents movement of the base 200 in an inferior direction (e.g., towards the lower anchoring assembly 112). The lock 224 permits, however, movement of the base 200 in a superior direction (e.g., away from the lower anchoring assembly 112, towards a head of the user 104 in operation) in the engaged position. In a disengaged position, the protrusions of the lock 224 are at least partially withdrawn from the channel, such that they no longer engage with the ratchet 228. The base 200 can then move in either direction along the rod 116. The lock 224 is biased towards the engaged position, e.g., with a spring or the like.

The base 200 can also, in some examples, include a slot 232 (in this example, the base 200 includes two slots 232) configured to receive a strap or sling (not shown). The strap or sling can assist application of the device 100 to the user 104, e.g., by suspending the device 100 from one or both shoulders, or from the neck, of the user 104 before the belts 124 and 136 are fastened.

Turning to the lower anchoring assembly 112, as shown in FIG. 2 the plate 132 includes a base 236, and a pad 240. The pad 240 can be mounted to the base 236 at an adjustable angle 242, e.g., by rotating about a pivot 244 defined by the base 236. The plate 132 can include a bias element such as a coil spring between the base 236 and the pad 240, e.g., to bias the pad 240 outwards from the base 236. As with the plate 120, the base 236 defines a raceway 248 to receive the belt 136, and one or more locking screws 252 (two are shown in this example) to secure the belt 136 within the raceway 248. The base 236 also includes a channel 256 to receive an inferior segment 260 (e.g., lower, towards the feet of the user 104 when the device 100 is in use) of the traction rod 116.

The segments 212 and 260 of the rod 116 can, in some examples, be formed as a single integrated rod. In this example, the segments 212 and 260 are separate to allow telescopic adjustment of the length of the rod 116, e.g., to accommodate various user heights. The segments 212 and 260 can also be coupled at a joint 264 that allows some angular deflection between the segments 212 and 260 (e.g., up to about ten degrees), to better conform to the shape of the user's back 128. The rod 116 can be fabricated from any material sufficiently stiff to substantially resist deformation when the device 100 is applying traction to the user 104 (e.g., to compress no more than about one percent of the total length of the rod 116, and/or to flex no more than about five degrees).

In some examples, the position of the lower anchoring assembly 112 along the rod 116 can be adjusted, via adjustment of the plate 132 along the rod 116. For example, the device 100 can include one or more (two are shown in this example) locks 268 supported by the plate 132 and configured to engage apertures 272 in the inferior segment 260 of the rod 116. The locks 268 prevent movement of the plate 132 along the segment 260 of rod 116 when engaged, and permit movement of the plate 132 along the segment 260 when disengaged. The locks 268 can therefore be employed to adjust the position of the lower anchoring assembly 112 to accommodate various user heights, in addition to or instead of the telescopic adjustment mentioned above. In other examples, the lower segment 260 can include a ratchet similar to the ratchet 228 for adjusting the position of the plate 132. In such examples, the locks 268 can serve to permit only movement in an inferior direction when engaged, and to permit movement of the plate 132 in either direction when disengaged.

Figure 3A:
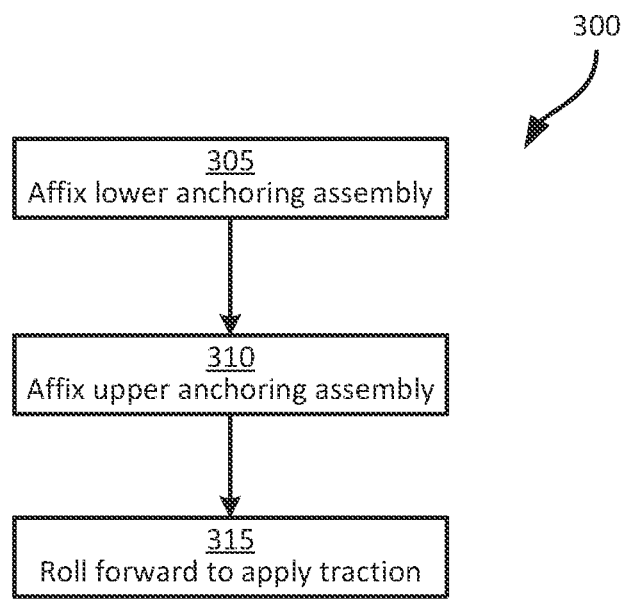
FIG. 3A is a flow chart of a method of applying and activating the device of FIG. 2.
Figure 3B:
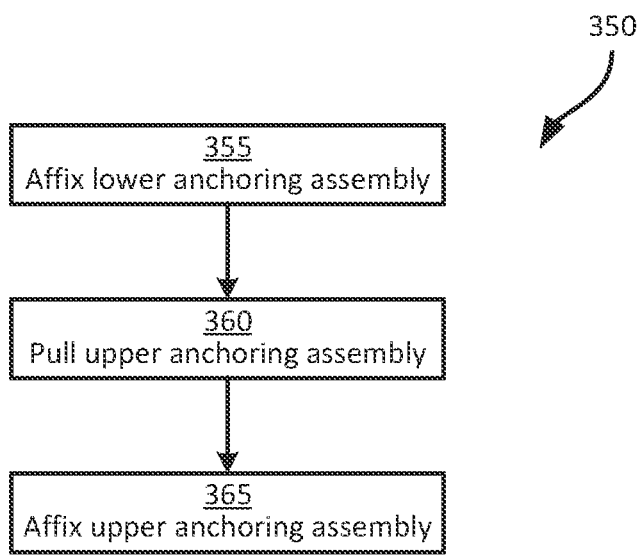
FIG. 3B is a flow chart of another method of applying and activating the device of FIG. 2.

Turning to FIG. 3A and FIG. 3B, various methods of operating the device 100, e.g., by the user 104, are discussed. FIG. 3A illustrates a first method 300 of applying and activating the device 100 (e.g., to apply spinal traction to the user 104). At block 305, the lower anchoring assembly 112 is affixed to the user 104, e.g., by fastening the belt 136 around the user's waist as shown in FIG. 1. At block 310, the upper anchoring assembly 108 is affixed to the user 104, e.g., by fastening the belt 124 around the user's chest as shown in FIG. 1. Blocks 305 and 310 can be performed in the opposite order than that shown in FIG. 3A, in other examples. The slot(s) 232 can be employed to hang the device 100 from one or both shoulders of the user 104 via straps or slings, until at least one of the belts 124 and 136 is fastened.

Once the belts 124 and 136 are fastened, at block 315 the user 104 can roll forward (e.g., apply spinal flexion) to increase the distance between the plates 120 and 132. The lock 224, in the engaged position, permits superior movement of the plate 120, and resists inferior movement of the plate 120 along the rod 116. Thus, when the user 104 returns to an upright position, the plate 120 remains at the increased distance, thus applying traction to a portion of the user's spine (e.g., resisting spinal compression resulting from the weight of the user's torso by transferring the weight to the belt 136 and the user's hips).

While applying spinal flexion at block 315, the user 104 can hold the lower anchoring assembly 112 in place by hand, e.g., to prevent the lower anchoring assembly 112 from sliding upwards along the torso of the user 104. In other examples, a strap can be mounted to a slot on the inferior side of the plate 132 (similar to the slots 232), with a length sufficient to reach the user's feet. By stepping on the strap, the lower anchoring assembly can be maintained in position while traction is applied at block 315.

Figure 4:
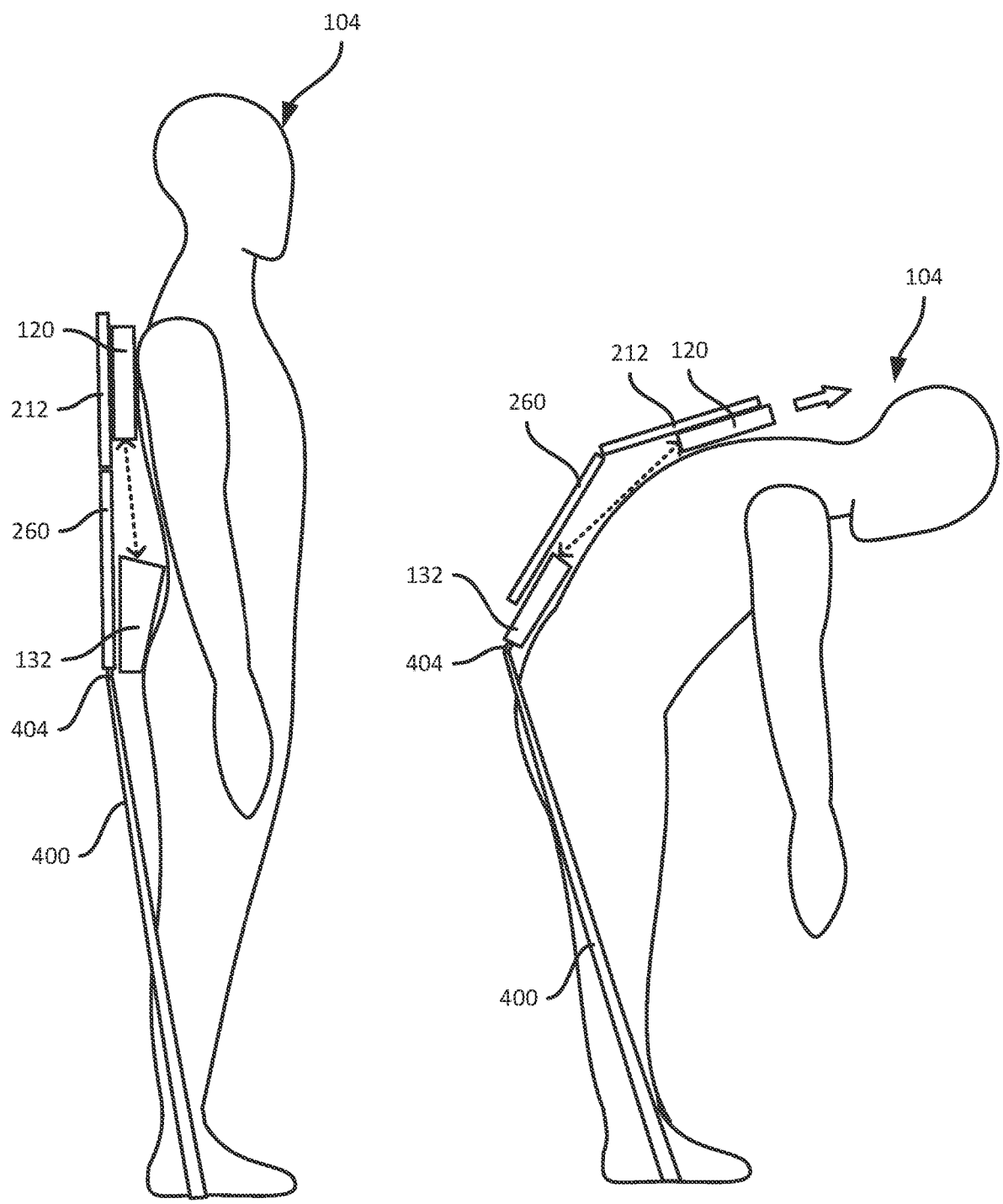
FIG. 4 is a diagram of an example performance of the method of FIG. 3A.

FIG. 4 illustrates an example activation of the device 100 via the method 300. In particular, as shown in the left portion of FIG. 4, in an initial position, the device 100 is affixed to the user 104. When first affixed to the user 104, the device 100 applies little or no traction. As shown in the right portion of FIG. 4, when the user rolls forward (range of motion exaggerated for illustrative purposes), the distance between the plates 120 and 132 is increased, and the ratchet subsequently maintains the increased distance when the user 104 returns to an upright position. As shown in FIG. 4, a strap 400 extending from a slot 404 or other fixture on the plate 132 can extend under the feet of the user 104 to prevent the plate 132 from sliding up the user's back.

Figure 5:
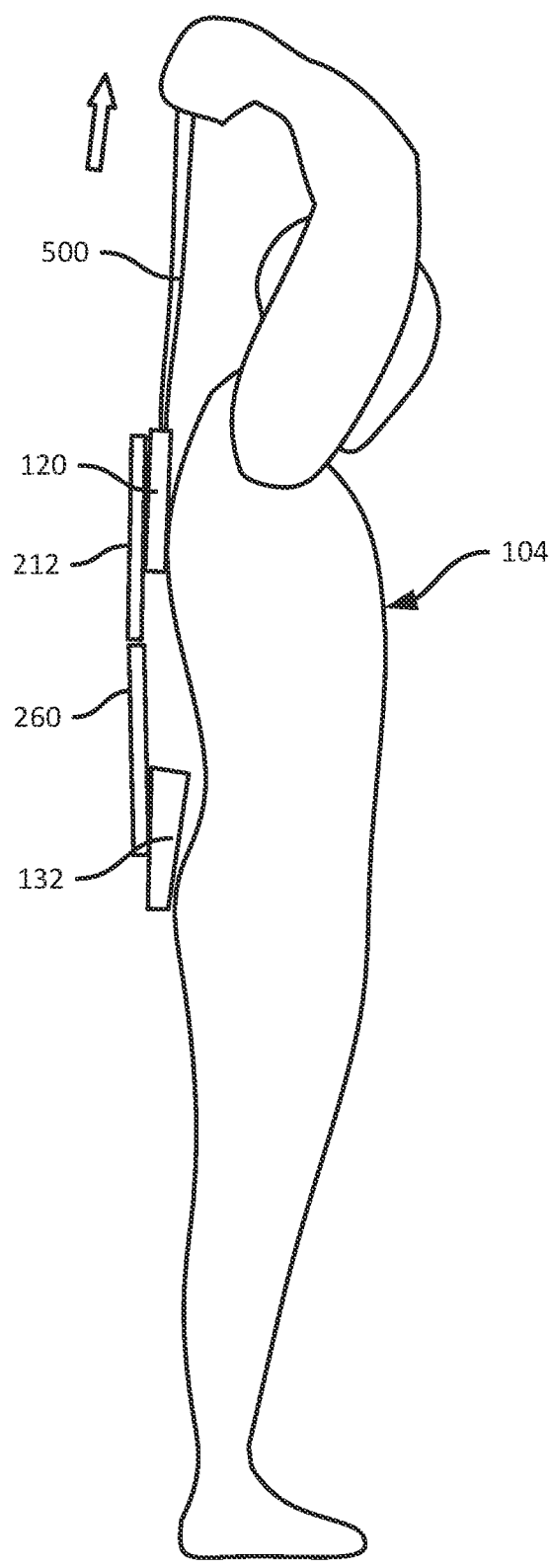
FIG. 5 is a diagram of an example performance of the method of FIG. 3B.

Returning to FIG. 3B, a further method 350 of applying and activating the device 100 is illustrated. At block 355, the lower anchoring assembly 112 is affixed to the user 104, as noted above in connection with block 305. The upper anchoring assembly 108 can be fastened loosely, but is not affixed at this point. At block 360, the upper anchoring assembly 108 is pulled, e.g., overhead by the user 104, to move the upper anchoring assembly 108 in a superior direction along the rod 116. Once the position of the upper anchoring assembly 108 has been set, the upper anchoring assembly 108 can be affixed at block 365, e.g., by tightening the belt 124. FIG. 5 illustrates an example performance of block 360, in which the user pulls overhead on the upper anchoring assembly, e.g., via a strap or sling 500 mounted to the plate 120 via one or more slots 232.

The scope of the claims should not be limited by the embodiments set forth in the above examples, but should be given the broadest interpretation consistent with the description as a whole.

The invention claimed is:

1. A wearable traction device, comprising:
   a traction rod including a superior segment, and an inferior segment;
   a lower anchoring assembly coupled to the inferior segment of the traction rod, the lower anchoring assembly configured for affixing to a lower torso of a user;
   an upper anchoring assembly movably coupled to the superior segment of the traction rod, the upper anchoring assembly configured for affixing to an upper torso of the user;
   a releasable lock supported on the upper anchoring assembly, the releasable lock having:
      (i) an engaged position configured to permit movement of the upper anchoring assembly in a superior direction along the superior segment of the traction rod, and prevent movement of the upper anchoring assembly in an inferior direction along the superior segment, and
      (ii) a disengaged position configured to permit movement of the upper anchoring assembly in the superior and inferior directions.

2. The wearable traction device of claim 1, wherein the lower anchoring assembly and the upper anchoring assembly each include:
   a traction plate coupled to the traction rod, and configured to rest against a back of the user; and
   a belt coupled to the traction plate, and configured to extend around a torso of the user.

3. The wearable traction device of claim 2, wherein the traction plate of the lower anchoring assembly further includes:
   a base coupled to the traction rod; and
   a pad mounted to the base at an adjustable angle relative to the base.

4. The wearable traction device of claim 3, wherein the traction plate of the lower anchoring assembly further includes a bias member biasing the pad away from the base.

5. The wearable traction device of claim 2, wherein the belt of each anchoring assembly includes a pocket configured to receive a reinforcing member.

6. A method of activating the wearable traction device of claim 1, the method comprising:
   affixing the lower anchoring assembly to the lower torso of the user;
   affixing the upper anchoring assembly to the upper torso of the user;
   subsequent to affixing the lower anchoring assembly and the upper anchoring assembly, applying traction to the upper anchoring assembly to move the upper anchoring assembly in the superior direction along the traction rod.

7. The method of claim 6, wherein applying traction includes performing a spinal flexion movement by the user.

8. The method of claim 6, wherein the method further comprises:
   after affixing the lower and upper anchoring assemblies, and prior to applying traction to the upper anchoring assembly, restricting movement of the lower anchoring assembly relative to the torso of the user.

9. The wearable traction device of claim 1, wherein the superior segment of the traction rod includes a ratchet, and wherein the releasable lock includes a protrusion configured to engage with the ratchet in the engaged position.

10. A method of activating the wearable traction device of claim 1, the method comprising:
    affixing the lower anchoring assembly to the lower torso of the user;
    subsequent to affixing the lower anchoring assembly, applying traction to the upper anchoring assembly to move the upper anchoring assembly in the superior direction along the traction rod; and
    subsequent to applying traction to the upper anchoring assembly, affixing the upper anchoring assembly to the upper torso of the user.

* * * * *